United States Patent [19]

Inoue et al.

[11] Patent Number: 5,398,686

[45] Date of Patent: Mar. 21, 1995

[54] MAGNETIC RESONANCE IMAGING APPARATUS

[75] Inventors: Hiroshi Inoue, Kyoto; Hirotsugu Mitsumata, Uji; Masami Sugie, Kusatsu; Osamu Sekiguchi, Kameoka, all of Japan

[73] Assignee: Shimadzu Corporation, Kyoto, Japan

[21] Appl. No.: 82,948

[22] Filed: Jun. 29, 1993

[30] Foreign Application Priority Data

Jun. 30, 1992 [JP] Japan .................................. 4-197877

[51] Int. Cl.6 .............................................. A61B 5/055
[52] U.S. Cl. ............................... 128/653.2; 128/653.5; 324/318
[58] Field of Search .......................... 128/653.2, 653.5; 324/318, 322, 309

[56] References Cited

U.S. PATENT DOCUMENTS

| | | |
|---|---|---|
| 4,629,989 | 12/1986 | Riehl et al. . |
| 4,684,894 | 8/1987 | Bliehall ............................ 128/653.5 |
| 4,727,328 | 2/1988 | Carper et al. . |
| 4,791,371 | 12/1988 | Krol ............................... 128/653.5 |
| 4,944,501 | 7/1990 | Sireul et al. . |
| 5,007,425 | 4/1991 | Vanek et al. . |
| 5,066,915 | 11/1991 | Omori et al. ......................... 324/318 |
| 5,085,219 | 2/1992 | Ortendahl et al. .................. 324/318 |
| 5,160,890 | 11/1992 | Roschmann ........................ 324/318 |
| 5,197,474 | 3/1993 | Englund et al. .................... 324/318 |
| 5,204,629 | 4/1993 | Ueyama ............................ 324/318 |
| 5,285,160 | 2/1994 | Loos et al. ........................ 128/653.5 |
| 5,293,126 | 3/1994 | Schaefer ............................ 324/318 |
| 5,311,134 | 5/1994 | Yamagata et al. ................ 128/653.5 |

FOREIGN PATENT DOCUMENTS 0187389 7/1986 European Pat. Off. .
0424808 5/1991 European Pat. Off. .

Primary Examiner—Krista M. Pfaffle
Attorney, Agent, or Firm—Nikaido, Marmelstein, Murray & Oram

[57] ABSTRACT

A gantry defines an opening, and a surface coil is mounted in a predetermined position inside the opening. In tomography using this MRI apparatus, an examinee supported on a top board is moved into the opening. At this time, the top board is movable without being obstructed by the surface coil. The surface coil receives NMR signals from a photographed site lying directly over the surface coil. Sectional images are prepared based on the NMR signals received. When shifting the site to be photographed, the operator in a scanner control room gives an instruction to move the top board, thereby adjusting a photographing position. It is unnecessary for the examinee to move on the top board, or for the operator to move from the scanner control room to the photographing room. The examinee entering the gantry opening is illuminated by light from a light projector. A position of the top board when the light illuminates the site to be photographed is regarded as a starting point. The top board is moved from the starting point by a distance between the light projector and surface coil. This achieves an accurate positional adjustment between the site to be photographed and the surface coil.

5 Claims, 3 Drawing Sheets

MAGNETIC RESONANCE IMAGING APPARATUS

BACKGROUND OF THE INVENTION

1. Field of the Invention

This invention relates to a magnetic resonance imaging apparatus (hereinafter referred to as an MRI apparatus) for obtaining sectional images of a desired site of an examinee. The sectional images are obtained by means of nuclear magnetic resonance signals (hereinafter referred to as NMR signals) released from the desired site of the examinee and received by a detecting surface coil in an opening of a gantry having a static magnetic field forming magnet and an inclined magnetic field coil.

2. Description of the Related Art

In an MRI apparatus for obtaining sectional images of a particular site such as the chest or the waist of an examinee, a surface coil is often employed for receiving the NMR signals since the surface coil provides excellent image quality and is easy to handle.

A conventional MRI apparatus using this type of surface coil includes, as main components thereof, a top board carrying the detecting surface coil, and a gantry defining an opening and having a static magnetic field forming magnet, an inclined magnetic field coil, a high frequency pulse generator and a signal transmitting coil. The apparatus further includes a vertically movable support for raising and lowering the top board and inserting the top board into the opening of the gantry, an image processor, and a system controller & RF unit.

Sectional images of a site of an examinee are obtained as follows.

First, the examinee is placed on the top board such that the site of the examinee to be photographed lies directly over the surface coil mounted in the top board. The top board is inserted into the opening of the gantry to a position in which the site of the examinee to be photographed lies centrally of the gantry.

Next, the inclined field coil is driven to superpose a linear magnetic field on a static magnetic field formed by the static magnetic field forming magnet, in order to provide positional information for use in tomographic image analysis. Then, the high frequency pulse generator is driven to generate high frequency pulses for exciting nuclear magnetic resonance in the examinee's body. NMR signals subsequently generated are received by the detecting surface coil.

Finally, the image processor prepares sectional images of the photographed site of the examinee based on the NMR signals received by the surface coil. The operations of the various components of the above apparatus are controlled by the system controller & RF unit.

However, with the construction having the detecting surface coil mounted in the top board, when photographs are taken of the site displaced from a sensitivity zone of the surface coil, or when a different site is to be photographed, the site must be positionally adjusted relative to the surface coil again. This requires the top board to be withdrawn from the opening of the gantry once to lift the examinee or shift the examinee on the top board, which could be painful to the examinee.

To solve such a problem, a type of MRI apparatus has been developed which includes a surface coil contained in a slide case mounted in the top board. The operator of the MRI apparatus manually moves the surface coil for positional adjustment between the surface coil and the site to be photographed.

According to this apparatus, a positional adjustment between the surface coil and the site to be photographed may be effected while the examinee lies in the opening of the gantry, and by moving the surface coil within the top board. Since it is unnecessary to move the examinee on the top board, the positional adjustment between the site and the surface coil may be carried out without distressing the examinee.

However, such an apparatus has the following disadvantage.

During a photographing operation, the operator controls a console or the like in a scanner control room which is partitioned from a photographing room in which the gantry and other equipment are installed. With the apparatus having the surface coil contained in the slide case, as noted above, the operator manually moves the surface coil for positional adjustment between the surface coil and the site to be photographed. To do this, the operator must move from the scanner control room to the photographing room. This imposes an irksome operation on the operator.

SUMMARY OF THE INVENTION

The present invention has been made having regard to the state of the art noted above. The object of the invention, therefore, is to provide a magnetic resonance imaging apparatus which allows the operator to carry out a positional adjustment between a site to be photographed and a surface coil with ease and without distressing the examinee.

The above object is fulfilled, according to the present invention, by a magnetic resonance imaging apparatus comprising a top board for supporting an examinee and movable into an opening of a gantry, and a detecting surface coil mounted in the opening for receiving nuclear magnetic resonance signals released from a photographed site of the examinee on the top board, thereby to obtain sectional images of the site of the examinee, wherein the surface coil is mounted in a predetermined position in the opening, the top board being movable close to the surface coil.

Specifically, the surface coil is positioned to receive the nuclear magnetic resonance signals with excellent sensitivity when the photographed site lies directly over the surface coil.

In the above construction, the surface coil is mounted in the predetermined position in the opening of the gantry, and the top board supporting the examinee is movable over the surface coil. Thus, a positional adjustment between the site to be photographed and the surface coil may be effected by moving the top board. The top board may be moved by the operator using a console or the like. It is unnecessary to shift the examinee on the top board, or for the operator to move from a scanner control room to a photographing room. The site to be photographed and the surface coil may be positionally adjusted relative to each other without distressing the examinee and without burdening the operator. This apparatus does not require a complicated construction such as a mechanism for sliding the surface coil by means of a slide case mounted in the top board.

The above magnetic resonance imaging apparatus may further comprise:
  a light projector for illuminating the examinee supported on the top board and entering the opening;
  indicating means for indicating that light from the light projector illuminates the site to be photographed of the examinee; and top board movement control means for determining a starting point based on a position of the top board at a time of indication by the indicating means, and effecting a control to move the top board from the starting point by a distance between the light projector and the surface coil.

As the top board carrying the examinee advances into the opening of the gantry, the light from the light projector illuminates the examinee successively from head to foot, for example. The operator observes the illuminated positions, and transmits an instruction from the indicating means when the light illuminates the site to be photographed. Upon receipt of the instruction from the indicating means, the top board movement control means regards a current position of the top board as a starting point, and causes the top board to move from the starting point by the distance between the light projector and the surface coil. The distance between the light projector and the surface coil, i.e. an amount of movement of the top board caused by the top board movement control means, is determined once the mounting position of the light project and that of the surface coil are determined. The top board moves under control of the top board movement control means, whereby the site to be photographed, which was confirmed by the position illuminated by the light projector, now lies directly over the surface coil. In this way, an accurate positional adjustment of the site to be photographed and the surface coil is effected.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DETAILED DESCRIPTION OF THE PREFERRED EMBODIMENTS

Preferred embodiments of this invention will be described in detail hereinafter with reference to the drawings.

First Embodiment

Figure 1:
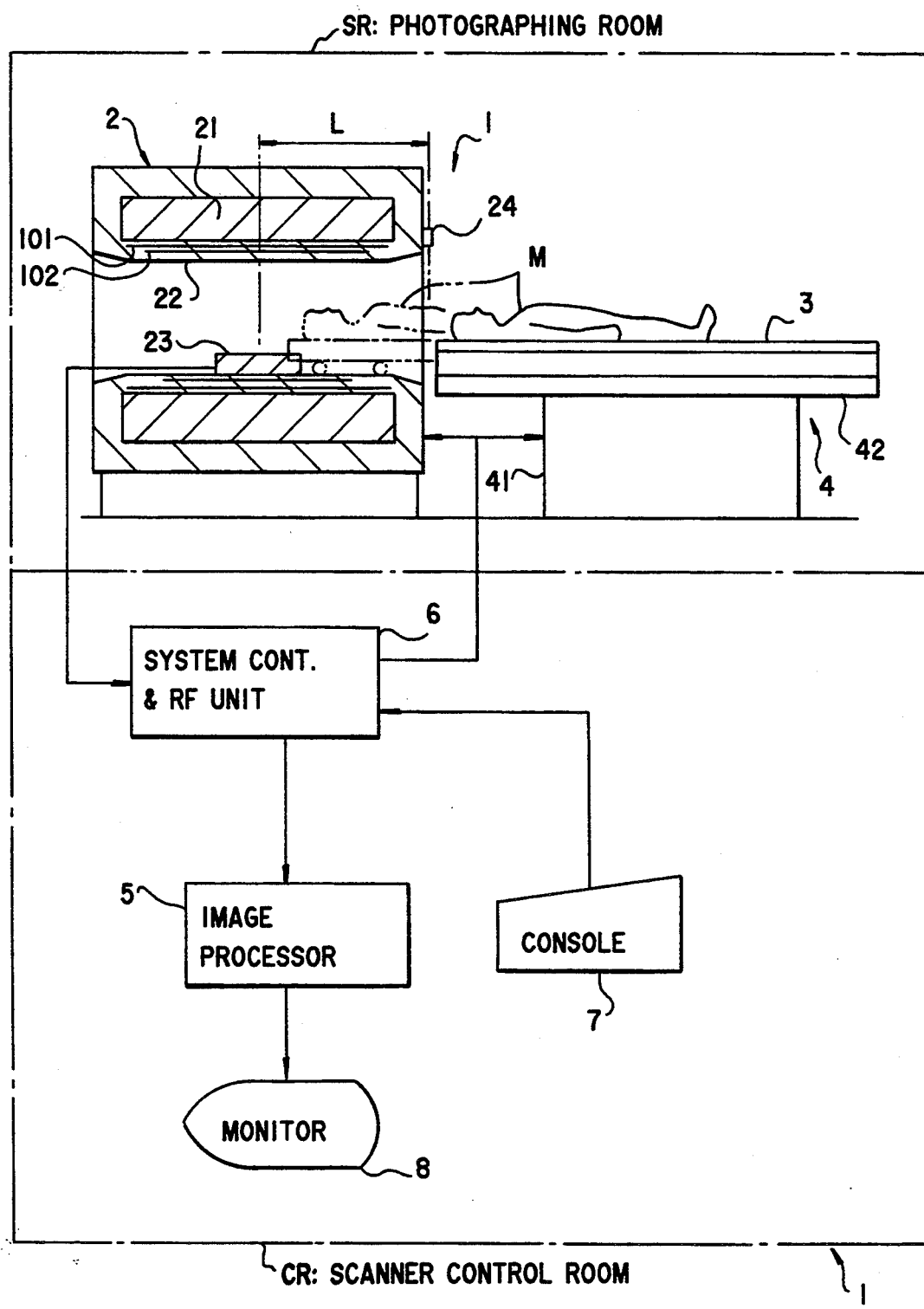
FIG. 1 is a view schematically showing a magnetic resonance imaging apparatus in a first embodiment of this invention.

A magnetic resonance imaging apparatus (MRI apparatus) in a first embodiment of this invention will be described with reference to FIGS. 1 through 3.

The MRI apparatus 1, broadly, includes a gantry 2 defining an opening, a top board 3 for supporting an examinee, a vertically movable support 4 for supporting and raising and lowering the top board 3 and inserting the top board 3 into the opening of the gantry 2, an image processor 5 for preparing sectional images of a photographed site based on NMR signals received, and a system controller & RF unit 6 for controlling operations of the components of the apparatus 1. These components will particularly be described below.

The gantry 2 defines a substantially circular opening 22 centrally thereof. In the opening 22 are a static magnetic field forming magnet 21 for forming a uniform static magnetic field, an inclined magnetic field coil 101, a high frequency pulse generator and a signal transmitting coil 102. An NMR signal receiving surface coil 23 is mounted in place inside the opening 22. This coil 23 is positioned on a bottom of the opening 22 to be suited to receive NMR signals with excellent sensitivity when a site to be photographed of an examinee M placed on the top board 3 lies directly over the surface coil 23. For example, the surface coil 23 should preferably have the center of reception sensitivity concurring with the center of the static magnetic field forming magnet 21 mounted in the gantry 2. A light projector 24 is attached to an upper position at a top board receiving end of the opening 22 for enabling a positional adjustment of the site to be photographed and the surface coil 23 to be carried out in a manner described hereinbelow.

Figure 3:
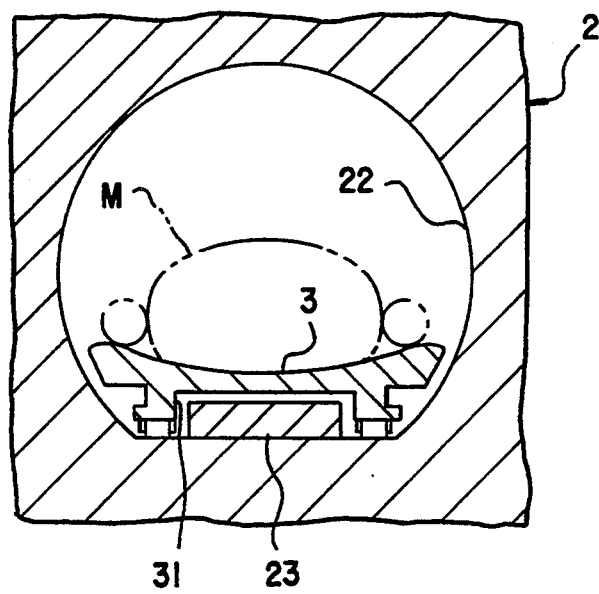
FIG. 3 is a sectional view on line 3—3 of FIG. 2.

As shown in FIG. 3, the top board 3 for supporting the examinee M on an upper surface thereof has a lower surface defining a longitudinal groove 31. This groove 31 allows the top board 3 inserted into the opening 22 of the gantry 2 to be moved to and fro in the opening 22 without contacting the surface coil 23 mounted to protrude inwardly of the opening 22.

The vertically movable support 4 has a vertically movable section 41 disposed adjacent the top board receiving end of the opening 22 of the gantry 2 for raising and lowering the top board 3. The support 4 further includes a moving section 42 mounted on the vertically movable section 41 for inserting the top board 3, as supported in a cantilever fashion, into the opening 22 of the gantry 2, and moving the top board 3 to and fro in the opening 22.

The image processor 5 obtains, through the system controller & RF unit 6, the NMR signals received by the surface coil 23, and prepares sectional images of the photographed site of the examinee M through predetermined arithmetic operations based on the data obtained. The images are displayed on a monitor 8.

The system controller & RF unit 6 controls the operations of the above components 2 to 5, e.g. starts and stops the static magnetic field forming magnet 21 and other coils mounted in the gantry 2, controls the vertically movable support 4 to move the top board 3 in the opening 22 of the gantry 2, and applies the NMR signals received by the surface coil 23 to the image processor 5.

The gantry 2, top board 3 and vertically movable support 4 are installed in a photographing room SR. The operator of the MRI apparatus 1 instructs the operations of the various components through a console 7 in a scanner control room CR which accommodates the image processor 5, system controller & RF unit 6 and console 7. These instructions are transmitted from the console 7 to the system controller & RF unit 6.

With the MRI apparatus 1 having the above construction, sectional images of a site of an examinee are obtained as follows.

First, the examinee M is placed on the top board 3 with his or her head directed toward the opening 22 of the gantry 2. Then, the vertically movable section 41 of the vertically movable support 4 is driven to raise the top board 3.

Next, the light projector 24 is driven to emit light while the top board 3 is inserted into the opening 22 of the gantry 2. At this time, as shown in a phantom line in FIG. 1, the light is emitted from the light projector 24 onto the examinee M placed on the top board 3. As the top board 3 advances into the opening 22, the light illuminates the examinee M successively from head to foot. The operator observes the illuminated positions, and transmits an instruction from the console 7 when the light illuminates the site to be photographed with the MRI apparatus 1. Upon receipt of the instruction from the console 7, the system controller & RF unit 6 regards a current position of the top board 3 as a starting point, and effects a control to move the top board 3 further from the starting point by a distance L (see FIG. 1) between the light projector 24 and the sensitivity center of the surface coil 23.

Figure 2:
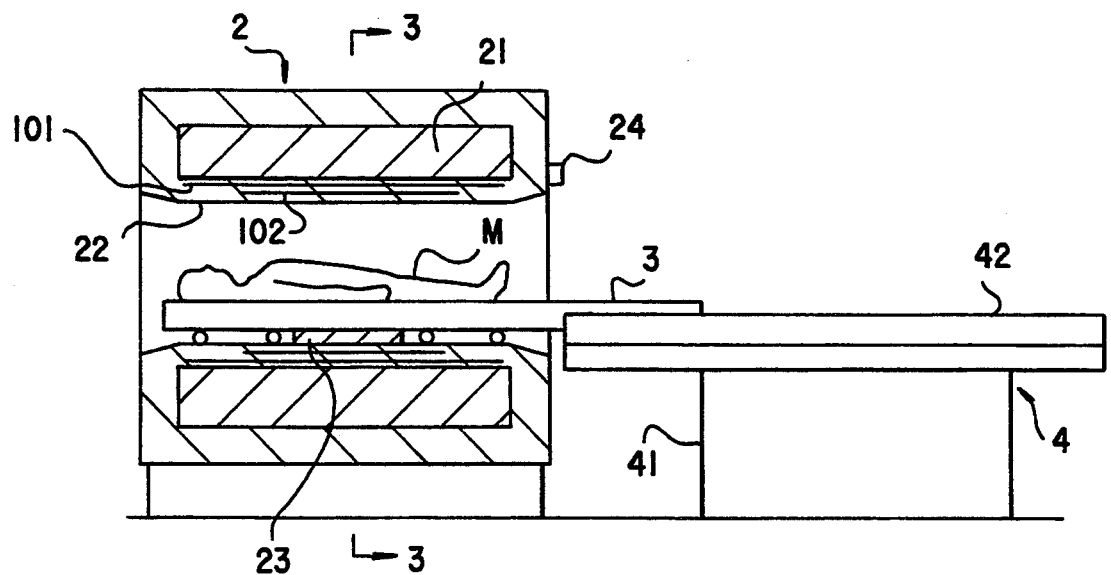
FIG. 2 is a view showing a state in which a positional adjustment between a site to be photographed and a surface coil has been completed.

When the top board 3, under control of the system controller & RF unit 6, has advanced the distance L from the starting point, the site to be photographed, which was confirmed by the position illuminated by the light projector 24, now lies directly over the sensitivity center of the surface coil 23 (see FIG. 2, in which the waist of the examinee is to be photographed). The amount of movement of the top board 3 from the starting point is specified when the light projector 24 and surface coil 23 are attached to the gantry 2.

Next, the inclined magnetic field coil is driven to superpose a linear magnetic field on the static magnetic field formed by the static magnetic field forming magnet 21, in order to provide positional information for use in tomographic image analysis. Then, the high frequency pulse generator is driven to generate high frequency pulses for exciting nuclear magnetic resonance in the examinee's body. The NMR signals subsequently generated are received by the surface coil 23.

The NMR signals received by the surface coil 23 are collected by the system controller & RF unit 6 and applied to the image processor 5. The image processor 5 prepares sectional images of the photographed site of the examinee based on the NMR signals received. These images are displayed on the monitor 8 or used otherwise.

When, for example, a shift of the site to be photographed is desired, the operator may remain in the scanner control room CR and adjust a photographing position. In this case, the operator, while referring to the sectional images displayed on the monitor 8, transmits an instruction from the console 7 to move the top board 3 an appropriate amount. It is thus unnecessary to relocate the examinee M on the top board 3, and the operator need not move from the scanner control room CR to the photographing room SR.

Second Embodiment

Figure 4:
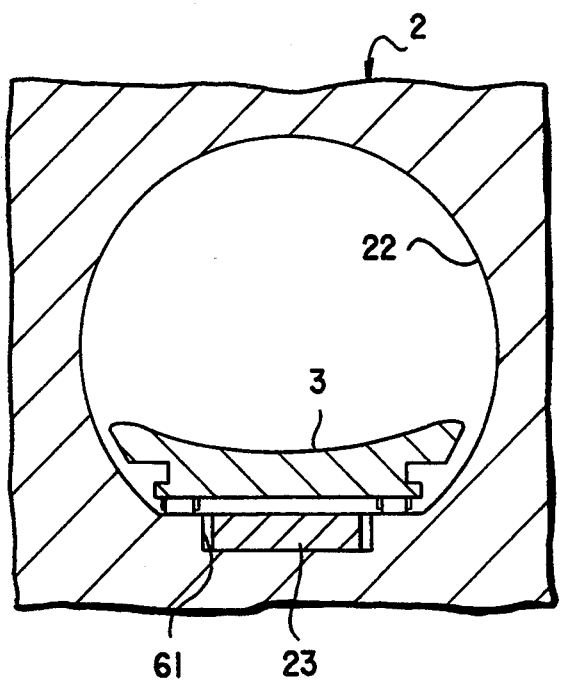
FIG. 4 is a sectional view showing a principal portion of a second embodiment.

An apparatus in a second embodiment of this invention will be described referring to FIG. 4.

In the second embodiment, the gantry 2 includes a recess 61 formed in a predetermined position in the opening 22. The surface coil 23 is mounted in the recess 61. With the surface coil 23 mounted in the recess 61, no projection due to the surface coil 23 is formed in the opening 22. Consequently, a top board 3 without the groove 31 formed in the lower surface thereof is movable in the opening 22 without being obstructed by the surface coil 23. The position of the recess 61 is the same as the position in which the surface coil 23 is mounted according to the first embodiment. The second embodiment is the same as the first embodiment in the photographing sequence and in the way the positional adjustment between the site to be photographed and the surface coil is carried out with reference to the position illuminated by the light projector 24.

Third Embodiment

Figure 5:
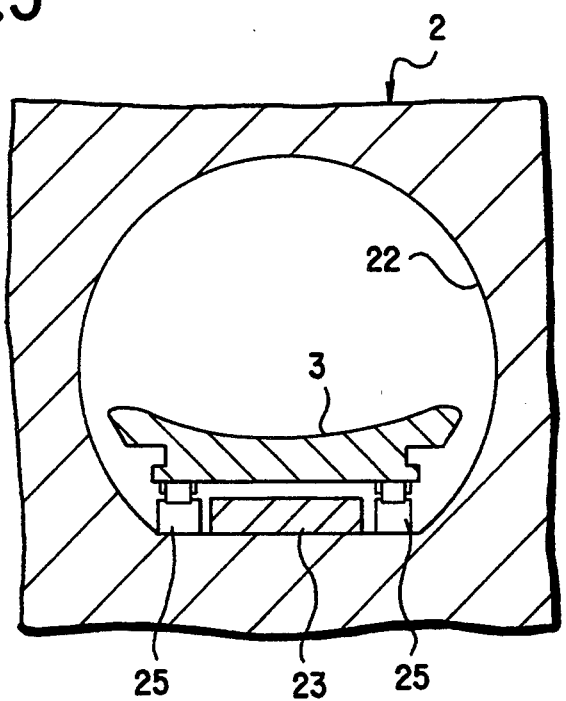
FIG. 5 is a sectional view showing a principal portion of a third embodiment.

Next, an apparatus in a third embodiment of this invention will be described referring to FIG. 5.

In the third embodiment, the gantry 2 includes a pair of rails 25 arranged in the opening 22. The rails 25 guide the top board 3 in its movement in the opening 22 of the gantry. The rails 25 have a sufficient height to avoid contact between the lower surface of the top board 3 in movement and the surface coil 23. With this construction, the top board 3 is movable in the opening 22 without being obstructed by the surface coil 23. The surface coil 23 is mounted in the same position as in the first embodiment. Further, the third embodiment is the same as the first embodiment in the photographing sequence and in the way the positional adjustment between the site to be photographed and the surface coil is carried out with reference to the position illuminated by the light projector 24.

The present invention may be embodied in other specific forms without departing from the spirit or essential attributes thereof and, accordingly, reference should be made to the appended claims, rather than to the foregoing specification, as indicating the scope of the invention.

What is claimed is:

1. A magnetic resonance imaging apparatus, comprising:
   a gantry having a static magnetic field forming magnet, an inclined magnetic field forming coil and a signal transmitting coil, said gantry also including an opening therein;
   a detecting surface coil stationarily disposed in a predetermined location on a lower inner peripheral surface of said opening for providing excellent sensitivity for photographing a portion of an examinee, said detecting surface coil for receiving nuclear magnetic resonance signals in said predetermined location;
   a top board for supporting said examinee, said top board being movable into and out of said opening in said gantry, such that said portion of said examinee supported on said top board is movable to a position above said detecting surface coil; and
   image processor means coupled to said detecting surface coil, said image processor means for generating sectional images based upon said nuclear magnetic resonance signals received by said detecting surface coil;
   wherein said nuclear magnetic resonance signals are released from a predetermined photographed site of the examinee, to obtain said sectional images after said nuclear magnetic resonance signals are processed by said image processor means.

2. A magnetic resonance imaging apparatus as defined in claim 1, said apparatus further comprising:
   a light projector for illuminating said examinee supported on said top board and entering said opening;
   indicating means for indicating that light from said light projector illuminates said photographed site of said examinee; and
   top board movement control means for determining a starting point based on a position of said top board at a time of indication by said indicating means, and controlling said top board to move from said starting point by a distance between said light projector and said surface coil.

3. A magnetic resonance imaging apparatus as recited in claim 1, wherein a lower surface of said top board includes a groove means formed therein, said groove means providing a clearance between the lower surface of the top board and the detecting surface coil.

4. A magnetic resonance imaging apparatus as recited in claim 1, wherein said gantry further comprises a recess formed in said inner peripheral surface of said opening, and wherein said detecting surface coil is mounted within said recess.

5. A magnetic resonance imaging apparatus as recited in claim 1, wherein said gantry includes rails disposed on said inner peripheral surface of said opening, said rails for engaging said top board and guiding said top board within said opening, and wherein said rails elevate said top board to provide a clearance between a lower surface of said top board and said detecting surface coil.

* * * * *